United States Patent [19]

Iton et al.

[11] Patent Number: 5,068,485

[45] Date of Patent: Nov. 26, 1991

[54] ACTIVATION OF METHANE BY TRANSITION METAL-SUBSTITUTED ALUMINOPHOSPHATE MOLECULAR SIEVES

[75] Inventors: Lennox E. Iton, Downers Grove; Victor A. Maroni, Naperville, both of Ill.

[73] Assignee: The United States of America as represented by the United States Department of Energy, Washington, D.C.

[21] Appl. No.: 494,380

[22] Filed: Mar. 16, 1990

[51] Int. Cl.$^5$ .......................... C07C 2/00; B01J 37/34
[52] U.S. Cl. ................................... 585/500; 585/514; 585/527; 585/531; 585/533; 585/700; 585/943; 502/5; 502/38; 502/514; 502/213; 502/208
[58] Field of Search ............... 585/500, 943, 700, 514, 585/527, 531, 533; 502/208, 213, 71, 77, 5, 38, 514

[56] References Cited

U.S. PATENT DOCUMENTS

| | | | |
|---|---|---|---|
| 4,310,440 | 1/1982 | Wilson et al. | 252/435 |
| 4,440,871 | 4/1984 | Lok et al. | 502/214 |
| 4,567,029 | 1/1986 | Wilson et al. | 423/306 |
| 4,793,984 | 12/1988 | Lok et al. | 423/306 |
| 4,973,777 | 11/1990 | Alagy et al. | 585/943 |

OTHER PUBLICATIONS

Iton et al., "Stabilization of Co(III) in Aluminophosphate Molecular Sieve Frameworks", Zeolites, 1989, vol. 9, Nov.

Nguyen et al., "Evidence For Activation Of Methane By Transition Metal-Substituted Aluminophosphate Molecular Sieves", American Chemical Society, 198th Meeting, Miami Beach, Fla., Sep. 10-15, 1989.

*Primary Examiner*—Anthony Mc Farlane
*Assistant Examiner*—Nhat Phan
*Attorney, Agent, or Firm*—Hugh W. Glenn; Robert J. Fisher; William R. Moser

[57] ABSTRACT

Aluminophosphate molecular sieves substituted with cobalt, manganese or iron and having the AlPO$_4$-34 or AlPO$_4$-5, or related AlPO$_4$ structure activate methane starting at approximately 350° C. Between 400° and 500° C. and at methane pressures $\leq 1$ atmosphere the rate of methane conversion increases steadily with typical conversion efficiencies at 500° C. approaching 50% and selectivity to the production of C$_{2+}$ hydrocarbons approaching 100%. The activation mechanism is based on reduction of the transition metal(III) form of the molecular sieve to the transition metal(II) form with accompanying oxidative dehydrogenation of the methane. Reoxidation of the - transition metal(II) form to the transition metal(III) form can be done either chemically (e.g., using O$_2$) or electrochemically.

14 Claims, 2 Drawing Sheets

ACTIVATION OF METHANE BY TRANSITION METAL-SUBSTITUTED ALUMINOPHOSPHATE MOLECULAR SIEVES

CONTRACTUAL ORIGIN OF THE INVENTION

The United States Government has rights in this invention under Contract No. W-31-109-ENG-38 between the U.S. Department of Energy and the University of Chicago, representing Argonne National Laboratory.

BACKGROUND OF THE INVENTION

This invention relates generally to a catalytic process capable of selectively producing a desired product from a given reactant and is particularly directed to the use of catalysts in the form of microporous crystalline solids, commonly referred to as molecular sieves.

The trend today in catalysis research is toward the development of the so-called "designer" catalysts, i.e., catalysts that will selectively produce the desired product from a given reactant. The class of materials that offers the greatest hope for designer catalysts is that which includes all the various types of molecular sieves. Molecular sieves are microporous crystalline solids composed of interconnecting channels and cavities. The microporous structure of molecular sieves provides a large, well defined internal surface area for catalysis or absorption and causes molecular sieves to be shape selective. Many types of molecular sieves with varying structures, pore sizes, combinations of framework atoms, and framework atom ratios have been either discovered or synthesized.

Included among the properties that cause molecular sieves to be promising for industrial applications are:
1. well defined crystal structure.
2. high internal surface area.
3. uniform pores with one or more discrete sizes.
4. good thermal stability.
5. exchangeable cations which can be used for catalysis; and
6. exchangeable framework metal atom chemistries.

Molecular sieves are classified according to the nature of their principal framework atoms, the ratio of these atoms, any substituent atoms present, and their pore size. The first three classifications determine the catalytic activity of the molecular sieve, while the pore size is important to the shape selectivity of the sieve.

There are three basic types of shape selectivity in molecular sieves. The first is reactant selectivity. If a reactant will not fit into the molecular sieve's pores, it cannot be catalyzed or absorbed by the internal sites. (It can, however, react with sites on the surface, but at a greatly reduced reactivity level because of the reduced number of such sites.) The second type of molecular sieve shape selectivity is transition state selectivity. If a reaction proceeds through a transition state that is too large to form within the molecular sieve's pores, the reaction cannot take place within the sieve. Finally, there is product selectivity. Any product formed must be small enough to diffuse out of the molecular sieve. Such shape selectivity constraints are very important to the designing of new catalysts for specific chemical synthesis.

Molecular sieves are usually synthesized by crystallization from a gel containing the desired framework atoms and a template, i.e., a molecule or molecular cation, usually organic, which determines the crystalline structure and pore size. The gel composition determines the framework atoms and their ratios. The template directs the crystallization process towards the desired sieve structures. After formation, the template is burned (calcined) away leaving an open pore structure.

The most well known class of molecular sieves is the zeolites. Zeolites are composed of silicon and aluminum atoms bridged by oxygen atoms in a tetrahedral arrangement. Zeolites have many different Si/Al atom ratios and pore sizes. Their catalytic activity is due to a charge imbalance at any Al-0-Si bonds. This imbalance creates negative charge in the framework which must be compensated by cations. When this cation is a proton, a Brønsted acid site is formed. Such sites are thought to be the main source of catalytic activity in the sieves, though other types of sites have been theorized. It should be noted that the sieve structure terminates in O—H bonds. Some of these exterior sites may catalyze reactions and are not subject to selectivity restrictions. However, these sites are generally not as reactive or as numerous as the intracrystalline Brønsted sites and, therefore, have only a small effect on reaction chemistry.

Another class of molecular sieves is the aluminophosphates ($AlPO_4$'s). These types of sieves, which are important to the present invention, are composed of aluminum(III) and phosphorous(V) atoms bridged by oxygen atoms and have $P(V)/Al(III) \approx 1$. However, $AlPO_4$ frameworks are neutrally charged and, therefore, exhibit little or no catalytic behavior. To create catalytic Brønsted sites in the $AlPO_4$'s, the Al(III) and/or P(V) positions are doped with a differently charged element, such as magnesium(II), manganese(II), cobalt(II), iron(II), zinc(II) or silicon(IV), where the divalent metals substitute for Al(III) while the silicon substitutes for P(V) in the $AlPO_4$ framework. These substitutions produce a negatively charged framework and Brønsted acid sites (see FIG. 1).

It has recently been reported that when Co(II) is substituted for Al(III) in the framework of certain aluminophosphate ($AlPO_4$) molecular sieves and the resulting Co(II)containing $AlPO_4$ (CoAPO) is calcined in oxygen, the Co(II) is oxidized to Co(III). Further work with these Co(III) CoAPOs showed that they possess strong oxidizing capability and, for example, can convert methanol to formaldehyde (at 25° C.), NO to $NO^+$ (at 25° C.), and $H_2$ to $2H^+$ (at $\geq$ 300° C.). See L. E. Iton, I. Choi, J. A. Desjardins and V. A. Maroni, *Zeolites* 9, 535 (1989).

The nature of the present invention is (1) the discovery that certain transition metal-substituted aluminophosphate ($AlPO_4$) molecular sieves can activate methane gas ($CH_4$) to produce $C_{2+}$ hydrocarbons at temperatures of 500° C. or less, (2) that the catalytic activity of these catalysts can be maintained using a variety of chemical and electrochemical methods, and (3) that product selectivity can be controlled by judicious selection of sieve pore structure and by integrated use of various combinations of molecular sieve materials.

OBJECTS AND SUMMARY OF THE INVENTION

Accordingly, it is an object of the present invention to provide a catalytic process particularly adapted for activating methane gas ($CH_4$) to produce $C_{2+}$ hydrocarbons at moderate temperatures.

Another object of the present invention is to provide a catalytic process based on a substituted aluminophosphate molecular sieve catalyst whose catalytic activity can be maintained using a variety of conventional chemical and electrochemical reoxidation methods.

Yet another object of the present invention is to provide a compact single-step process for transforming methane into a high-leverage fuel product and/or into one or more widely used industrial chemicals.

A further object of the present invention is to provide a catalytic process based on a bifunctional catalyst that promotes the dissociation of the C—H bonds of methane while simultaneously directing the ensuing chemical reactions to a wide range of highly desirable products.

It is another object of the present invention to provide a catalytic process based on a catalyst that operates efficiently under moderate conditions of temperature ($\leq 500°$ C.) and pressure ($\leq 10$ atm), and for extended periods of time, without need for frequent regeneration or replacement.

Accordingly, this invention contemplates an aluminophosphate molecular sieve catalyst substituted in the framework atom positions with cobalt, manganese, or iron, which is particularly adapted for activating methane and converting it to $-C_{2+}$ hydrocarbons, such as ethane and propane. The inventive catalytic process is capable of converting surplus natural gas, coal-derived methane, and other high volatility chemicals derived from coal conversion, to such widely used industrial products as liquified petroleum gas (LPG), light olefins (e.g., ethylene and propylene), gasoline-range products (i.e., hydrocarbons containing 6 to 10 carbon atoms per molecule), and important industrial intermediates such as xylenes, epoxides, aldehydes, and ketones. The use of this invention is thus consistent with present day thought on how best to utilize the current worldwide surplus of natural gas. Perhaps the most desirable commercial feature of the present invention is that it fosters the utilization of the many hundreds of TCUs (trillion cubic feet) of natural gas primarily in the form of methane that is tied in with coal and oil reserves in the United States.

BRIEF DESCRIPTION OF THE DRAWINGS

The appended claims set forth those novel features which characterize the invention. However, the invention itself, as well as further objects and advantages thereof, will be understood by reference to the following detailed description of a preferred embodiment taken in conjunction with the accompanying drawings, in which:

DETAILED DESCRIPTION OF THE PREFERRED EMBODIMENT

Figure 1:
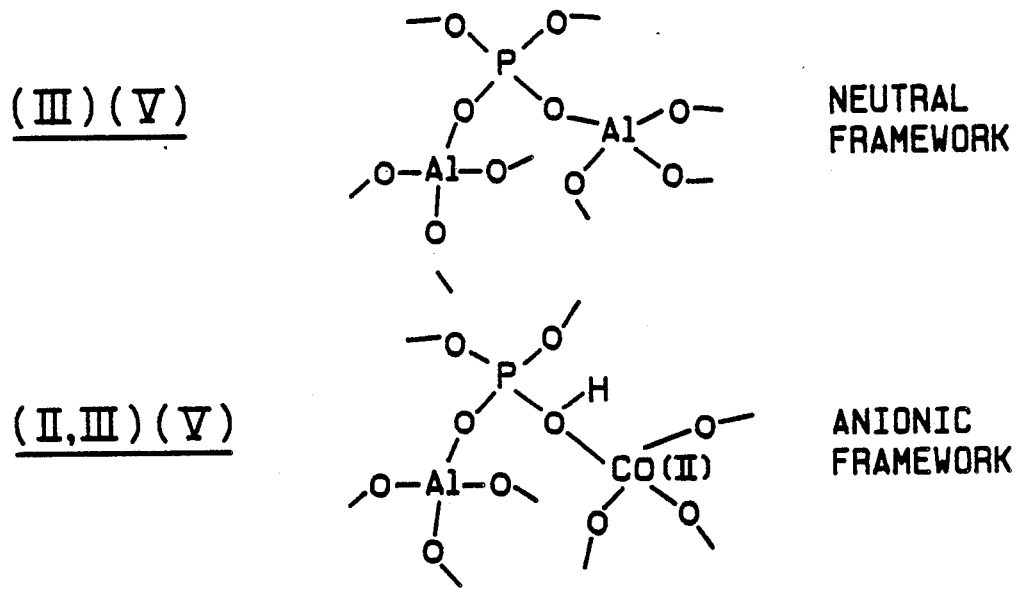
FIG. 1 illustrates the negatively charged framework and Bronsted acid sites produced in an $AlPO_4$ sieve structure by the substitution of divalent metals such as cobalt(II) for the aluminum(III) in the sieve framework.

The cobalt-substituted aluminophosphate materials were prepared using modifications of procedures described in U.S. Pat. Nos. 4,310,440 to Wilson et al., 4,440,871 to Lok et al., and 4,567,029 to Wilson et al. In each case, only samples free of detectable crystalline impurities (as indicated by x-ray powder diffraction patterns) were employed for the subsequent experiments. CoAPO-5 was synthesized from a gel made with aluminum oxide, using tetrapropylammonium hydroxide (TPA-OH) to provide the template. The cobalt was added via a solution of cobalt nitrate in phosphoric acid (P:Co = 48). CoAPSO-34 was synthesized from a gel made with aluminum isopropoxide and a colloidal silica sol (Ludox), using tetraethylammonium hydroxide (TEA-OH) to provide the template. The cobalt was added via a solution of cobalt nitrate in phosphoric acid (P:Co = 12). CoAPO-34 was prepared using aluminum oxide, TEA-OH, cobalt sulphate and $H_3PO_4$ (P:Co = 12) as described in the aforementioned U.S. Pat. No. 4,567,029. The as-synthesized materials were calcined in flowing air at 550° C to burn out the templating ions. Crystallinity and phase purity of both assynthesized and calcined materials were established by X-ray powder diffraction measurements.

Reactions of methane on the aforementioned molecular sieve materials and on several other metal oxides known to activate methane (e.g., $Sm_2O_3$) were carried out in a quartz tube reactor having an 8 mm inside diameter. The catalyst sample ($\sim 1$ gram) was supported on a quartz fritted disk fused into the midsection of the quartz tube. The tube was mounted in an electrically heated furnace (with the sample in the middle of the heated zone) and attached to the gas handling system. The gases used in the experiments [99.999% He, 10% $CH_4$ in Ar ($C_{2+}$ hydrocarbons/$CH_4 \simeq 0.002$) and "zero" air, all supplied by Matheson Gas Products] were introduced at the bottom of the reaction tube. A quartz-sheathed thermocouple was positioned inside the reaction tube just above the bed of catalyst material. Electrochemical activation was accomplished by inserting two coiled sections of platinum wire that were flattened to conform to the side wall of the reaction tube and then mounted in the tube so that they faced each other with a spacing of $\sim 3$ mm.

In a typical experiment with a molecular sieve material, the sieve sample was calcined in "zero" air at 550° C. in the reaction tube to burn off any remaining template ions (for a fresh sample) or carbonaceous residues (for a used sample). This calcining restored the cobalt-containing molecular sieves to the Co(III) form. After calcining, the reaction tube was brought to the desired temperature and purged of residual oxygen with flowing helium, then $\sim 10$ cc (STP) of the 10% $CH_4$ in Ar mixture was introduced at a rate of $\sim 0.5$ cc/min. The reaction products coming out the top of the reaction tube were collected in a liquid nitrogen cooled loop. The loop was then isolated from the reaction tube and warmed up to room temperature; after which a gas sample was withdrawn through a septum port on the side of the loop (using a gas syringe) and injected into a gas chromatograph (GC) equipped with a flame ionization detector (FID). In some experiments injections were also made into a GC equipped with a thermal conductivity detector (TCD) to determine the amounts of $H_2O$, $CO$, and $CO_2$ that were produced relative to the amount of $CH_4$ reacted.

Electrochemical activation studies were performed using a constant voltage power supply. Potentials in the range from 3 to 10 V dc were applied across the two platinum wire electrodes (described above). Gas handling procedures employed in the presence of an applied potential were the same as those used on air calcined molecular sieve samples, except that the sieve sample was fully reduced (deactivated) with CH$_4$ between the calcining and helium purging steps. The voltage was applied during purging and maintained throughout the CH$_4$ introduction step.

Methane activation experiments were performed on the following aluminophosphate molecular sieve materials: CoAPSO-34 (P:Co:Si = 12:1:1.8), CoAPO-5 (P:Co = 24:1), MAPO-5 (P:Mg =12:1) and SAPO-34 (P:Si = 6.7:1). The onset temperature for activation of CH$_4$ by the cobalt-containing AlPO$_4$ (i.e., where a few percent of C$_{2+}$ products are observed relative to the CH$_4$) occurs in the 350 to 400° C. range. At 500° C. the reaction proceeds more rapidly and single pass conversions of CH$_4$ to C$_{2+}$ hydrocarbons ranging from 15 to 30% were observed. In single pass experiments without electrochemical stimulation, ~1 cc (STP) of methane deactivates almost all of the active sites in ~1 gram of the CoAPSO-34 or CoAPO-5 used in this work and recalcination with O$_2$ is required to reactivate the sieve material. Many air calcinings have been run on some samples of CoAPSO-34 without evidence of significant permanent loss of activity, but in other cases we have observed steady decreases in activity with extended use. In the presence of applied dc potentials in the 3 to 10 V range, it is possible to activate the reduced form of the cobalt-containing molecular sieves [(HCo(II)APSO-34 and HCo(II)APO-5] and achieve significant ($\geq 15\%$) methane conversion to C$_{2+}$ hydrocarbons in a single pass at 500° C. However, even the electrochemically activated samples tended to exhibit reduced activity with extended use.

Identical experiments were performed on the silicon-substituted AlPO$_4$-34 (SAPO-34) and magnesium-substituted AlPO$_4$-5 (MAPO-5), wherein air calcination and electrochemical stimulation were employed in the same manner as was used with the CoAPSO-34 and CoAPO-5. None of these experiments gave any evidence of methane activation to C$_{2+}$ hydrocarbons. A test of air-calcined Sm$_2$O$_3$, a known methane activation catalyst at $\geq 700°$ C., failed to produce any C$_{2+}$ products in the test apparatus for temperatures up to 580° C., using methane only as a reactant (no oxygen co-feed).

Data from comparative experiments —— CoAPSO-34 vs. SAPO-34 and CoAPO-5 vs. MAPO-5 —— show that cobalt is essential to the activation process. The oxidation state chemistry and chemical substitutability of manganese and iron indicates that these transition metals likewise could be incorporated into the frameworks of aluminophosphate molecular sieves to produce the type of catalyst upon which the present invention is based.

Our prior work indicates that the active state of the cobalt is tetrahedrally-coorindated Co(III) bound in the framework metal atom positions of the molecular sieve. The overall reaction mechanism is believed to include the following steps:

$$2CH_4 + 2Co(III)APO \rightarrow C_2H_6 + 2HCo(II)APO \quad [1]$$

$$C_2H_6 + 2Co(III)APO \rightarrow C_2H_4 + 2HCo(II)APO \quad [2]$$

$$2HCo(II)APO \xrightarrow[\text{electric field}]{O_2 \text{ or}} 2Co(III)APO + H_2O \text{ or } H_2. \quad [3]$$

The formation of C$_3$ hydrocarbons could occur from reaction of methyl radicals (CH$_3$·) with ethylene or from Brønsted acid catalyzed reactions involving ethylene. All of the above reactions are believed to be directed by the molecular sieve framework.

Although it is assumed that the framework-bound cobalt is the active agent in this catalysis, there was evidence that air calcined and electrochemically stimulated beds of Co(II)-exchanged SAPO-34 and Co(II)-exchanged Y zeolite also produced detectable quantities of C$_{2+}$ hydrocarbons when exposed to methane at 500° C. This apparent catalytic activity of Co(II)-exchanged molecular sieves is believed to occur by a mechanism that is separate from, but possibly related to, the one given above for framework-bound Co(II)/Co(III) in AlPO$_4$ molecular sieve structures.

The results presented above give clear evidence that cobalt-substituted aluminophosphate molecular sieves have the capability to catalyze the coupling of methane to C$_{2+}$ hydrocarbons at temperatures $\leq 500°$ C. The single-pass yields which have exceeded 30% at 500° C., the high selectivity to C$_{2+}$ hydrocarbons, the encouraging observation that molecular oxygen is not essential to the activation process, and the absence of large quantities of CO$_x$ in the product stream represent a significant advance in the state of the art for methane coupling using inorganic catalyst materials. The further finding that the cobalt-substituted molecular sieves can be maintained in the active state by an electric field allows for the development of continuous methane homologation processes using, e.g., packed or fluidized electrochemical bed reactors.

Figure 2:
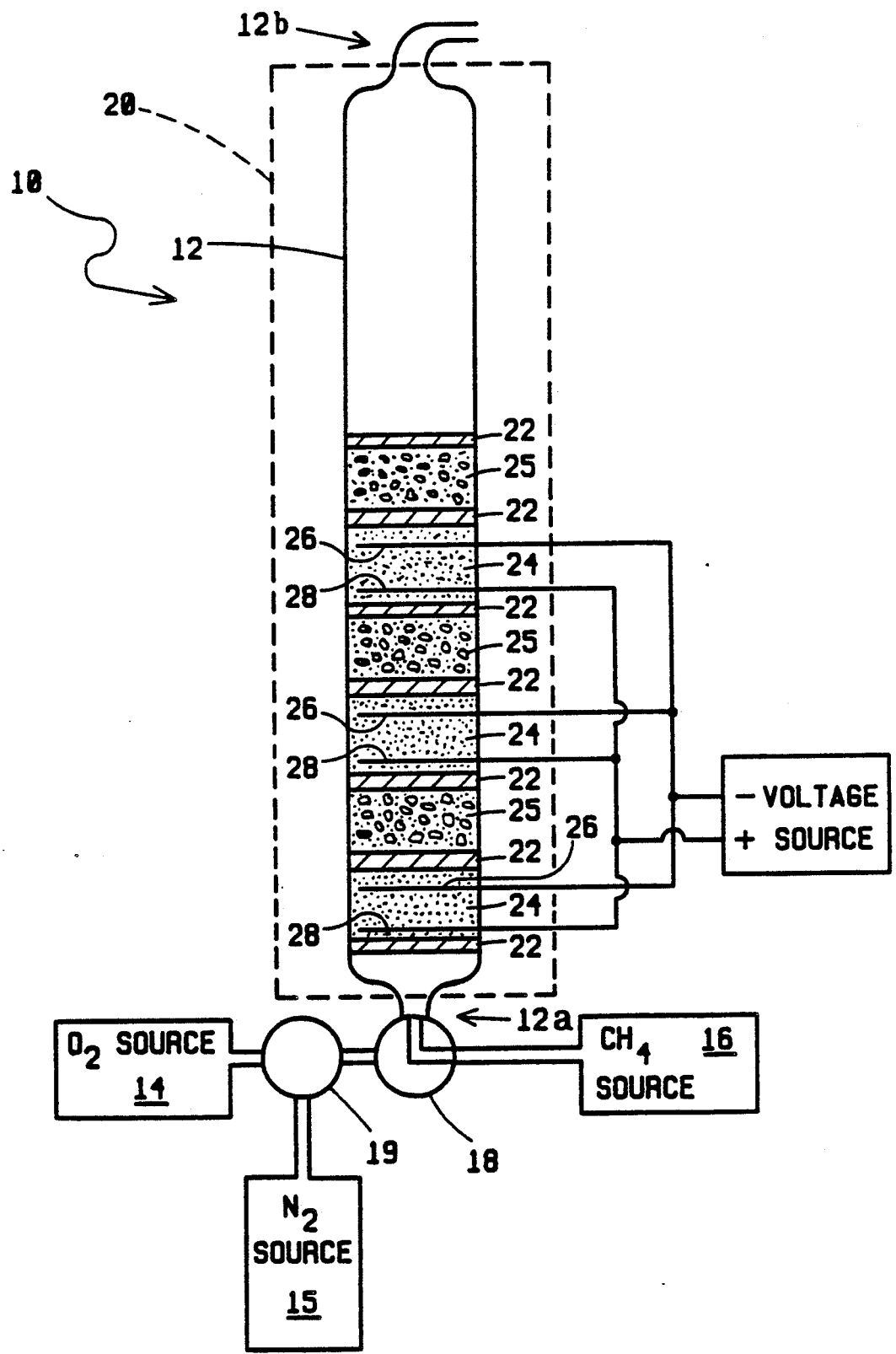
FIG. 2 is a simplified schematic diagram of a multistage, multicatalyst, packed-bed column for the conversion of natural gas (primarily methane) to $C_6$–$C_{10}$ hydrocarbons using a medium pore size, transition metal-substituted aluminophosphate molecular sieve catalyst together with an olefin homologation catalyst.

Referring to FIG. 2, there is shown a simplified schematic diagram of a multi-stage, multi-catalyst, packed-bed column 10 for use in the conversion of natural gas (primarily methane) to C$_6$-C$_{10}$ hydrocarbons using a medium pore size transition metal substituted aluminophosphate molecular sieve catalyst together with an olefin homologation catalyst, such as Mobil's H-ZSM-5. The multi-stage, packed-bed column 10 includes a ceramic or glass reactor tube 12 having an inlet end 12a and an outlet end 12b. Coupled to the inlet end 12a of the reactor tube 12 is a rotatable valve 18. Coupled to the rotatable valve 18 is an O$_2$ source 14, an N$_2$ source 15, and a CH$_4$ source 16. The rotatable valve 18 permits either oxygen, nitrogen, or methane to be provided to the inlet end 12a of the reactor tube 12. Another valve 19 connects either the O$_2$ source 14 or the N$_2$ source 15 to the reactor tube 12.

Disposed along the length of the reactor tube 12 in a spaced manner are a plurality of separator layers 22. Each of these separator layers 22 is preferably comprised of an inert porous material such as a ceramic screen or a stainless steel mesh. Also disposed along the length of the reactor tube 12 in a spaced manner intermediate to adjacent separator layers 22 are a plurality of catalyst layers 24. Each of the catalyst layers 24 is preferably comprised of either a manganese, iron or cobalt substituted aluminophosphate molecular sieve material as previously described. Also disposed along the length of the reactor tube 12 in a spaced manner are a plurality of layers of H-ZSM-5 25 which are also disposed between adjacent separator layers 22. A pair of negative and positive electrodes 26 and 28 are each disposed within a respective aluminophosphate molecular sieve catalyst layer 24 and are coupled to a voltage source 30. The electrodes are preferably in the form of a thin mesh and are comprised of platinum. The tube reactor 12 is disposed within an electric heater 20. The multi-stage, packed bed column 10 converts methane to $C_6$–$C_{10}$ hydrocarbons by oxygen calcination, electrochemical stimulation, or chemical stimulation in the following manner. The methane is introduced into the tube reactor 12 at pressures $\leq$ 1 atmosphere.

The multi-stage, packed-bed column 10 can be operated in a continuous mode wherein the methane is continuously fed to the reactor through the inlet 12a and an electric field is applied between the negative and positive electrodes 26 and 28 and across the catalyst layers 24.

The substituted aluminophosphate molecular sieve material may also be activated by chemical regeneration in the following manner. The methane may be directed through the quartz reactor tube 12, followed by an intermittent flow of oxidant provided to the inlet end 12a of the reactor tube 12 and an oxidant clearing pulse using an inert gas, such as $N_2$. In this approach, the methane and oxidant are alternately provided to the reactor tube 12, with the methane oxidatively coupled to $C_{2+}$ hydrocarbons and the cobalt in the molecular sieve material reduced from the trivalent to the divalent state. Upon providing an oxidant to the reactor tube 12, the cobalt in the molecular sieve material is reoxidized from the divalent to the trivalent state. This alternating procedure may be continued indefinitely to maintain and utilize the catalytic activity of the transition metal-substituted $AlPO_4$ molecular sieve.

As shown in FIG. 2 and as described above, H-ZSM-5, an aluminosilicate zeolite, is disposed intermediate adjacent layers of the medium pore size transition metal-substituted aluminophosphate molecular sieve material layers 24 in the tube reactor 12. The transition metal-substituted aluminophosphate molecular sieve material is particularly useful in converting methane to the lighter hydrocarbons, i.e., alkanes and alkenes, while the H-ZSM-5 zeolite is particularly useful in homologating the olefins from the transition metal-substituted aluminophosphate stage to $C_6$–$C_{10}$ hydrocarbons.

There has thus been identified a specific type of catalyst and shown a catalytic process for converting methane to heavier hydrocarbons, which employs a transition metal-substituted aluminophosphate molecular sieve for activating the methane gas at temperatures of 500° or less. The aluminophosphate molecular sieve is substituted with either cobalt, manganese or iron and includes $AlPO_4$-34, or $AlPO_4$-5, or possibly other $AlPO_4$ structures capable of activating methane starting at approximately 350° C.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. A process for converting methane ($CH_4$) to $C_{2+}$ hydrocarbons using a molecular sieve having a template, said process comprising the steps of:
    calcining a transition metal-substituted aluminophosphate molecular sieve at 500–550° C. in flowing air to remove the template or any coke that is present and to oxidize the transition metal to the trivalent state, wherein the transition metal is selected from the group consisting of cobalt, manganese or iron and the aluminophosphate molecular sieve is either $AlPO_4$-34 or $AlPO_4$-5 or equivalent $AlPO_4$ structure;
    passing $CH_4$ over the aluminophosphate molecular sieve at 400 to 500° C., whereby the transition metal is reduced to a divalent state and the $CH_4$ is converted to $C_{2+}$ hydrocarbons.

2. The process of claim 1 further comprising the step of directing the $CH_4$ through a plurality of said transition metal-substituted aluminophosphate molecular sieves arranged in a spaced array.

3. The process of claim 2 further comprising the step of passing the $C_{2+}$ hydrocarbons through a homologation catalyst containing a zeolite to obtain $C_6$–$C_{10}$ hydrocarbons, wherein the zeolite is arranged in a plurality of spaced layers and each zeolite layer is disposed between adjacently spaced $AlPO_4$ molecular sieve layers.

4. The process of claim 3 wherein said zeolite is comprised of H-ZSM-5.

5. The method of claim 4 further comprising the step of passing the $CH_4$ through a plurality of porous separator layers each disposed between adjacent transition metal-substituted aluminophosphate molecular sieves and layers of H-ZSM-5.

6. The process of claim 1 wherein the $CH_4$ is directed through the transition metal-substituted aluminophosphate molecular sieve at a pressure $\leq$ 1 atmosphere.

7. The process of claim 1 further comprising the step of activating the transition metal-substituted aluminophosphate molecular sieve, wherein the activation includes directing an oxidant through the sieve to re-oxidize the aluminophosphate molecular sieve.

8. The method of claim 7 wherein the oxidant is selected from the group consisting of air, $O_2$, ozone or hydrogen peroxide.

9. The process of claim 7 wherein the $CH_4$ and oxidant are directed through the transition metal-substituted aluminophosphate molecular sieve simultaneously.

10. The process of claim 7 wherein the $CH_4$ and oxidant are directed through the transition metal-substituted aluminophosphate molecular sieve in a sequential, alternating manner.

11. The process of claim 1 further comprising the step of activating the transition metal-substituted aluminophosphate molecular sieve, wherein the activation involves applying an electric field across the sieve.

12. The process of claim 11 wherein the electric field is on the order of 10 volts.

13. The method of claim 11 wherein the electric field is applied by incorporating first and second electrodes within the sieve in a spaced manner and applying a voltage difference between said first and second electrodes.

14. The process of claim 13 further comprising the step of providing first and second electrodes disposed within the transition metal-substituted aluminophosphate molecular sieve in a spaced manner, wherein said electrodes are comprised of platinum.

* * * * *